US010940172B2

(12) United States Patent
Caldwell et al.

(10) Patent No.: US 10,940,172 B2
(45) Date of Patent: Mar. 9, 2021

(54) METHODS OF FEEDING ANIMALS PHYTOGENIC PRODUCTS

(71) Applicant: PURINA ANIMAL NUTRITION LLC, Shoreview, MN (US)

(72) Inventors: James D. Caldwell, St. Clair, MO (US); Bill L. Miller, Labadie, MO (US)

(73) Assignee: PURINA ANIMAL NUTRITION LLC, Arden Hills, MN (US)

( * ) Notice: Subject to any disclaimer, the term of this patent is extended or adjusted under 35 U.S.C. 154(b) by 284 days.

(21) Appl. No.: 15/397,461

(22) Filed: Jan. 3, 2017

(65) Prior Publication Data
US 2018/0185425 A1 Jul. 5, 2018

(51) Int. Cl.
A61K 36/185 (2006.01)
A61K 36/53 (2006.01)
A61K 36/81 (2006.01)
A61K 36/9066 (2006.01)
A23K 50/10 (2016.01)
A23K 10/30 (2016.01)
A23K 20/10 (2016.01)

(52) U.S. Cl.
CPC ............ A61K 36/185 (2013.01); A23K 10/30 (2016.05); A23K 20/10 (2016.05); A23K 50/10 (2016.05); A61K 36/53 (2013.01); A61K 36/81 (2013.01); A61K 36/9066 (2013.01)

(58) Field of Classification Search
None
See application file for complete search history.

(56) References Cited

U.S. PATENT DOCUMENTS

| | | | |
|---|---|---|---|
| 2,125,398 A | 8/1938 | Reichert et al. | |
| 4,378,376 A | 3/1983 | Wagner et al. | |
| 4,617,190 A | 10/1986 | Montgomery | |
| 4,961,934 A | 10/1990 | Iwasaki et al. | |
| 5,085,873 A | 2/1992 | Degre | |
| 5,580,592 A | 12/1996 | Nassauer et al. | |
| 5,607,681 A | 3/1997 | Galley et al. | |
| 5,668,299 A | 9/1997 | Debonte et al. | |
| 5,747,078 A | 5/1998 | De et al. | |
| 5,756,132 A | 5/1998 | Rebhan | |
| 5,785,990 A | 7/1998 | Langrehr | |
| 5,792,501 A | 8/1998 | Lepine | |
| 5,795,602 A | 8/1998 | Craig et al. | |
| 5,830,511 A | 11/1998 | Mullerat et al. | |
| 5,861,187 A | 1/1999 | Debonte et al. | |
| 5,962,062 A | 10/1999 | Carrie et al. | |
| 6,348,223 B1 | 2/2002 | Claycamp et al. | |
| 6,541,047 B1 | 4/2003 | Claycamp et al. | |
| 7,709,033 B2 | 5/2010 | Kvist et al. | |
| RE43,929 E | 1/2013 | Miller et al. | |
| 8,349,313 B2 | 1/2013 | Smith et al. | |
| 2002/0018828 A1 | 2/2002 | Lepine | |
| 2002/0119136 A1 | 8/2002 | Johansen | |
| 2005/0171367 A1 | 8/2005 | Deloach | |
| 2006/0159728 A1 | 7/2006 | Miller | |
| 2006/0289354 A1 | 12/2006 | Zhou et al. | |
| 2007/0036850 A1 | 2/2007 | Roehrich et al. | |
| 2007/0134369 A1 | 6/2007 | Mazeris | |
| 2007/0203802 A1 | 8/2007 | Medo et al. | |
| 2007/0209599 A1* | 9/2007 | Block | A23K 50/00 119/51.01 |
| 2008/0026036 A1 | 1/2008 | Miller et al. | |
| 2008/0026101 A1 | 1/2008 | Nickel et al. | |
| 2009/0253790 A1 | 10/2009 | Smith et al. | |
| 2009/0317378 A1 | 12/2009 | Perraudin | |
| 2010/0221386 A1 | 9/2010 | Buysse et al. | |
| 2011/0201081 A1 | 8/2011 | Kensch et al. | |
| 2011/0229598 A1 | 9/2011 | Musser | |
| 2013/0280369 A1 | 10/2013 | Miller | |
| 2014/0147548 A1 | 5/2014 | Miller et al. | |

(Continued)

FOREIGN PATENT DOCUMENTS

CA 2323581 A1 10/1999
CN 101049116 A 10/2007

(Continued)

OTHER PUBLICATIONS

"A Guide to Calf Milk Replacers—Types, Use and Quality", Bovine Alliance on Management & Nutrition, 2008.
"Jersey Blend—Cow's match—Calf growth formula", Jan. 1, 2004, Mar. 2013, XP55194288, Retrieved from the Internet:URL:http://www.lolmilkreplacer.com/stellen/groups/public/documents/web_content/ecmp2-0186429.pdf, 2 pages.
"K-Cal for Calves Energy Supplement", from hllps://www.savacaf.com/producls/k-cal-for-calves-energy-supplement/, 2007.
"Manual on the Use of the LP-System in Milk Handling and Preservation", 1999, 4 pages.
"MIA-A", from hllps://www.mrclab.com/dala/producls/MIA-S-30_0PR.pdf, 2005.

(Continued)

Primary Examiner — Russell G Fiebig
(74) Attorney, Agent, or Firm — Dorsey & Whitney LLP

(57) ABSTRACT

A method of feeding a non-livestock ruminant animal a feed composition including a phytogenic composition for improving performance during periods of heat stress involves determining the non-livestock ruminant animal is experiencing heat stress during a period of heat stress conditions, and feeding the heat stressed non-livestock ruminant animal the feed composition including an amount of the phytogenic composition that is effective to improve performance. A method of feeding a non-livestock ruminant animal a feed composition including a phytogenic composition for improving performance in anticipation of periods of heat stress involves determining a potential for heat stress is increased based on one or more of historical weather patterns or short-term forecasts, and feeding the non-livestock ruminant animal the feed composition including the phytogenic composition based on the determined potential for heat stress.

13 Claims, 5 Drawing Sheets

(56) References Cited

U.S. PATENT DOCUMENTS

| | | | | |
|---|---|---|---|---|
| 2015/0374740 | A1* | 12/2015 | Forsberg | A61K 33/06 424/94.61 |
| 2017/0202928 | A1 | 7/2017 | Miller et al. | |
| 2017/0231254 | A1 | 8/2017 | Miller | |

FOREIGN PATENT DOCUMENTS

| | | | | |
|---|---|---|---|---|
| CN | 101703171 | A | | 5/2010 |
| CN | 101911981 | A | | 12/2010 |
| CN | 102132766 | A | | 7/2011 |
| CN | 102805263 | A | | 12/2012 |
| CN | 103271091 | A | | 9/2013 |
| CN | 104621047 | A | * | 5/2015 |
| CN | 106260523 | A | * | 1/2017 |
| EP | 0229938 | A1 | | 7/1987 |
| EP | 0282663 | B1 | | 12/1991 |
| EP | 0642740 | B1 | | 3/1995 |
| EP | 1637880 | A1 | | 3/2006 |
| EP | 1815754 | A1 | | 8/2007 |
| JP | 2509932 | Y2 | | 2/1990 |
| JP | H0789863 | | | 10/1995 |
| JP | 3145829 | U | | 3/2001 |
| JP | 2002544212 | A | | 12/2002 |
| JP | 2004236552 | A | | 8/2004 |
| KR | 20100101091 | A | | 9/2010 |
| WO | 9949740 | A1 | | 10/1999 |
| WO | 0069267 | A1 | | 11/2000 |
| WO | 02056879 | A1 | | 7/2002 |
| WO | 2007015937 | A1 | | 2/2007 |
| WO | 2007106452 | A2 | | 9/2007 |
| WO | WO-2007106452 | A2 | * | 9/2007 ............ A23K 50/30 |
| WO | 2011055387 | A2 | | 5/2011 |
| WO | 2011061756 | A2 | | 5/2011 |
| WO | 2015160818 | A1 | | 10/2015 |

OTHER PUBLICATIONS

"Milk Balancer Can Help When Feeding Wasting Milk", Dairy Business East www.dairybusiness.com, Feb. 2015, p. 12.

"mM vs ppm", retrieved from Internet, Jun. 2016.

"New Dairy Calf Production Products that can Increase Your Profit", by Milk Specialties Global Naimal Nutrition, PM Primer™, PM Balancer™ downloaded from www.progressivedairy.com on Mar. 5, 2015., p. 83.

"Nursing Formula Select", Available online at www.masterfeeds.com on Sep. 2, 2011.

"Pasteurized Milk Balancer", Available online at https://s3.amazonaws.com, 2009.

"The Science of Mixing Milk Replacer", from http://calfsessions.com/2013/06/science-mixing-milk-replacer-rnixology-101/, 2013.

"Use of the Brix Refractometer for Monitoring Milk Total Solids and Colostrum Quality", Available online at www.rnilkproductsinc.com on Dec. 5, 2011.

"Yeast Cell Wall", European Association for Specialty Yeast Products, Nov. 5, 2015, 1 page.

Barabas, J, "An alternative method of milk treatment", http://www.fao.org/ag/aga/frg/feedback/war/v6200b/v6200b0t.htm, Sep. 13, 1994, 5 pages.

Better Crops, "Phosphorus in Animal Nutrition", Better Crops, 1999, vol. 83. No. 1 pp. 32-33.

Campbell, R E. et al., "The use of lactoperoxidase for the bleaching of fluid whey", Journal of Dairy Science, 2012, 95.6, pp. 2882-2890.

Connor, William, "Am. J Clin. Nutr", 1999, 69: 827-828.

Costello, "Milk Extenders and Fortifiers—with downloadable calculator", Available online at www.calfsessions.com, Jan. 2015.

Coverdale, et al., "Effect of Various Levels of Forage and Form of Diet on Rumen Development and Growth in Calves", J. Dairy Sci., 2004, vol. 87 pp. 2554-2562.

Crews, D H. et al., "Journal of Animal Science", Animal Genetics: Division Editor Cell Biology S. Ellis Associate Editor Growth and Developmental Biology S. Johnson Calvert Associate Editor M. Estienne Associate Editor J. Matte Associate Editor J. O'Doherty, XP055426140,, Retrieved from the Internet: URL:http://www.jtmtg.org/JAM/2012/abstracts/2012-JAMAbstracts.pdf [retrieved on Nov. 17, 2017], Jan. 1, 2012, p. 116.

De Halleux, V et al., "Variability in human milk composition: benefit of individualized fortification in very-low-birth-weight infants'", The American Journal of Clinical Nutrition, 2013, vol. 98(suppl) pp. 529S-535S.

Drackley, Jim, "Replacing Milk-Derived Proteins and Carbohydrates in Milk Replacer", University of Illinois at Urbana-Champaign, Department of Animal Sciences, May 29, 2013.

Dumitrascu, Loredana et al., "Thermal Inactivation of Lactoperoxidase in Goat, Sheep and Bovine Milk—A Comparative Kinetic and Thermodynamic Study", Journal of Food Engineering, 2012, vol. 113, pp. 47-52.

Elizondo-Salazar, J. A. et al., "Pasteurization of Non-Saleable Milk", Penn State Extension, Department of Animal Science, DSE 2013-187, originally published as DAS 07-121, updated on Aug. 23, 2013, May 2007.

Fathi, M. H. et al., "The effect of vanilla flavoured calf starter on performance of Holstein calves", Journal of Animal and Feed sciences, 2009, vol. 18, pp. 412-419.

Godden, S, "A review of issues surrounding the feeding of waste milk and pasteurization of waste milk and colostrum", College of Veterinary Medicine, University of Minnesota, Sep. 2005, 13 pages.

Gouveia, et al., Brazilian Journal of Microbiology, 2013, 44, 2, pp. 499-504.

Griffiths, "Improving the Safety and Quality of Milk: Milk Production and Processing Woodhead Publishing Series in Food ScienceTechnology and Nutrition", Apr. 21, 2010, 295 pages.

Heinrichs, et al., Journal of dairy science, Dec. 2003, vol. 86, No. 12, pp. 4064-9.

Hill, S R. et al., "Effects of Milk Replacer Composition on Growth, Body Composition, and Nutrient Excretion in Preweaned Holstein Heifers", Journal of Dairy Science, American Dairy Science Association, US, Aug. 1, 2008, vol. 91, No. 8, pp. 3145-3155.

Jackett, et al., "Virulence of *Mycobacterium tuberculosis* and Susceptibility to Peroxidative Killing Systems", Journal of General Microbiology, 107(2):273-278.

Jorgensen, M et al., "On-Farm Pasteurization of Milk for Calves", University of Wisconsin Dail)'Update, Dail)' Team Extension, Mar. 31, 2005, pp. 1-3.

Langendijk, et al., "Effects of pre- and postnatal exposure to garlic and aniseed flavour on pre- and postweaning feed intake in pigs", Livestock Science, Elsevier Amsterdam, NL, Apr. 29, 2007, vol. 108, No. 1-3, pp. 284-287.

Mitsuru, Kamiya et al., "Effects of feeding level of milk replacer on body growth, plasma metabolite and insulin concentrations, and visceral organ growth of suckling calves", Animal Science Journal XP055194192, ISSN: 1344-3941, DOI: 10.1111/j.1740-0929.2009.00690.x, Dec. 2009, vol. 80, No. 6 pp. 662-668.

Montoro, C et al., "Effect of flavoring a starter in a same manner as a milk replacer on intake and performance of calves", Animal Feed Science and Technology, Feb. 28, 2011, vol. 164, pp. 130-134.

Moore, D A. et al., "Quality assessments of waste milk at a calf ranch", J. Dairy Sci, 2009, vol. 92 pp. 3503-3509.

Mullan, W .M.A., "Manufacture of milk powders containing a functional LP system", [Online]. Available from: htt.Q://www.dairyscience.info/exploitation-of-ant-microbial-proteins/168-lactoperoxidase-system.html. Accessed: Jan. 10, 2014. Revised Aug. 2009, 2003.

Nabte-Solfs, Luis A., "Effect of 13-Mannanase Enzyme Addition to Soy-Containing Milk Replacers on Growth and Health of Neonatal Dairy Calves", Thesis Presented to the Faculty of the Graduate School of Cornell University, Jan. 2009.

Oostindjerm, et al., "Prenatal flavor exposure affects growth, health and behavior of newly weaned piglets", Physiology and Behavior, Elsevier Science Ltd., Oxford, GB, Apr. 19, 2010, vol. 99, No. 5, pp. 579-586.

Pruitt, K. M. et al., "Quantitative analysis of bovine lactoperoxidase system components and of ti1e effects of the activated system on bacterial growth and survival", Indigenous antimicrobial agents of

(56) References Cited

OTHER PUBLICATIONS milk. Recent developments, Uppsala (Sweden) Aug. 31-Sep. 1993, FIL-IDF. Secretariat general, 1994.

Riley, et al., "Penetration of hydrogen peroxide from contact lenses or tear-side solution into the aqueous humor", Optom Vis Sci., 1991, 68:7,546-551.

Rochow, N. et al., "Target Fortification of Breast Milk with Fat, Protein, and Carbohydrates for Preterrn Infants", The Journal of Pediatrics, 2013, vol. 163, No. 4, pp. 001-1007.

Rudolph, Bryan, "Phytase use in pig feed: a real profitability boost", All About Feed, 2014, vol. 22 No. 8, pp. 22-24.

Russell, N. J. et al., "in Food Preservatives ISBN 0-306-47736-X", 2003.

Sebastian, S et al., "Apparent Digestibility of Protein and Amino Acids in Broiler Chickens Fed a Com-Soybean Diet Supplemented with Microbial Phytase", Department of Animal Science, Macdonald Campus of McGill University, 1997, 76{12}: 1760-9.

Selia, Jane et al., "Engineering Aspects of Milk and Dairy Products", CRC Press, 2010, pp. 222.

Siemens, M et al., "Managing and feeding Holstein steers: birth to 350 lbs", US Dept. of Agriculture, Univ. of Wisconsin-Extension. Publication A3662. Board of Regents of the Univ. of Wisconsin System, 1996, pp. 1-6, specif. pp. 1, 3, 4.

Smith, Daniel L. et al., "The Effect of Mannan Oligosaccharide Supplementation on Body Weight Gain and Fat Accrual in C57BI/6J Mice", Obesity (Silver Spring), doi:10.1038/oby.2009.308, May 2010, 18(5):995-999.

Stone, Bill, "Waste milk, milk replacer or pasteurized waste milk", The Manager, Jun. 2004.

Touchette, K. J. et al., "Liquid Egg as an Alternative Protein Source in Calf Milk Replacers", J. Dairy Sci., 2003, 86:2622-2628.

Yang, et al., "Study on the Colostrum Preservation of Milk Cows by Utilizing the Lactoperoxidase System", Guizhou Agricultural Sciences, accessed Dec. 28, 2013., May 2007.

Echternkamp, S.E. , "Relationship between placental development and calf birth weight in beef cattle", Animal Reproduction Science, 32: 1-13, 1993.

Fao Animal Production and Health, , "Rearing Young Ruminants on Milk Replacers and Starter Feeds", 2011, 1-79.

Euro Food Safety Auth., Scientific opinion on the safety and efficacy of RonozymeHiPhos M/L (6-phytase) as a feed additive for poultry and pigs, EFSA Journal; 10(1):2527, 2012, 12 pages.

Tomkins, T. et al., "Milk replacer research leads to new developments", Feedstuffs, Oct. 10, 1994, pp. 13-15 and 23.

* cited by examiner

METHODS OF FEEDING ANIMALS PHYTOGENIC PRODUCTS

TECHNICAL FIELD

Implementations relate to feed products and methods of feeding such products to ruminant animals. More particularly, implementations provide methods of feeding non-domesticated, non-livestock ruminant animals feed compositions supplemented with phytogenic additives to improve performance during, or in anticipation of, periods of heat stress.

BACKGROUND

Ruminant animals, such as deer, often live in uncontrolled environments, exposed to a wide range of unpredictable conditions that may impact animal health. Among these conditions, variations in temperature may be especially harmful and/or difficult to combat. High temperatures and/or humidity levels may cause ruminant animals to experience heat stress, a health condition associated with a range of interrelated symptoms that may include reduced feed intake, malnutrition, weight loss, and/or illness. Indeed, heat stress is a major cause of death for ruminant animals, especially non-livestock, non-domesticated ruminants, for which artificial cooling techniques and facilities may be impractical and expensive. The lack of feasible approaches for treating heat stress in such animals may strain both the economy and various environmental ecosystems. Thus, improved methods of treating heat stress in ruminant animals in a non-invasive manner that neither imposes lifestyle restrictions on the animals nor relies on temperature-controlled facilities or cooling devices may be desired.

SUMMARY

In some embodiments, a method of feeding a non-livestock ruminant animal a feed composition including a phytogenic composition for improving performance during periods of heat stress may involve determining the non-livestock ruminant animal is experiencing heat stress during a period of heat stress conditions, and feeding the heat stressed non-livestock ruminant animal the feed composition including an amount of the phytogenic composition that is effective to improve performance.

In certain implementations and alternatives, the method may further involve determining a potential for heat stress is increased based on one or more of historical weather patterns or short-term weather forecasts, and feeding the non-livestock ruminant animal the feed composition including the phytogenic composition based on the determined potential for heat stress. In such embodiments, feeding the non-livestock ruminant animal the feed composition based on the determined potential for heat stress may cause the animal to avoid developing one or more symptoms of heat stress.

In some examples, the phytogenic composition may include at least one of quillaja, *curcuma*, cayenne pepper, or thyme oil. In some embodiments, the phytogenic composition may comprise about 0.008 to about 0.064 wt % of the feed composition.

In certain implementations and alternatives, determining the non-livestock ruminant animal is experiencing heat stress may involve observing at least one of a decrease in feed intake, reduced activity levels, open mouth breathing, increased panting, sweating, or reduced reproduction. In some examples, the amount of the phytogenic composition effective to improve performance may be from about 100 milligrams to about 1500 milligrams of the phytogenic composition per ruminant per day. In some embodiments, improved performance may include one or more of increased body weight, increased rib flesh, or increased feed intake. In certain implementations and alternatives, improved performance may include an approximately 30 percent increase in daily feed intake compared to a non-livestock ruminant animal not fed the feed composition including the amount of the phytogenic composition that is effective to improve performance.

In some embodiments, the non-livestock ruminant animal may be a non-domesticated animal of the family Cervidae. In some examples, the non-livestock ruminant animal may be an adult white-tailed deer. In some embodiments, the non-livestock ruminant animal may be a breeding-age doe.

In certain implementations and alternatives, the feed composition may further include a base feed, the base feed including one or more of processed grain by-products, roughage products, plant protein products, grain products, molasses products, pellet binders, vegetable oils, salt, calcium carbonate, probiotics, flavoring agents, vitamins, or minerals. In some examples, the base feed and the phytogenic composition may be mixed together by an end user to form the feed composition. In such embodiments, prior to the step of feeding, the base feed and the phytogenic composition may be integrally mixed. In some examples, feeding the heat stressed non-livestock ruminant animal the feed composition may involve providing the feed composition on an ad libitum basis.

In some embodiments, a method of feeding a non-livestock ruminant animal a feed composition including a phytogenic composition for improving performance in anticipation of periods of heat stress may involve determining a potential for heat stress is increased based on one or more of historical weather patterns or short-term forecasts, and feeding the non-livestock ruminant animal the feed composition including the phytogenic composition based on the determined potential for heat stress.

In certain implementations and alternatives, an amount of the phytogenic composition may be from about 100 milligrams to about 1500 milligrams of the phytogenic composition per ruminant per day. In some examples, the phytogenic composition may include at least one of quillaja, *curcuma*, cayenne pepper, or thyme oil.

DETAILED DESCRIPTION

Figure 1:
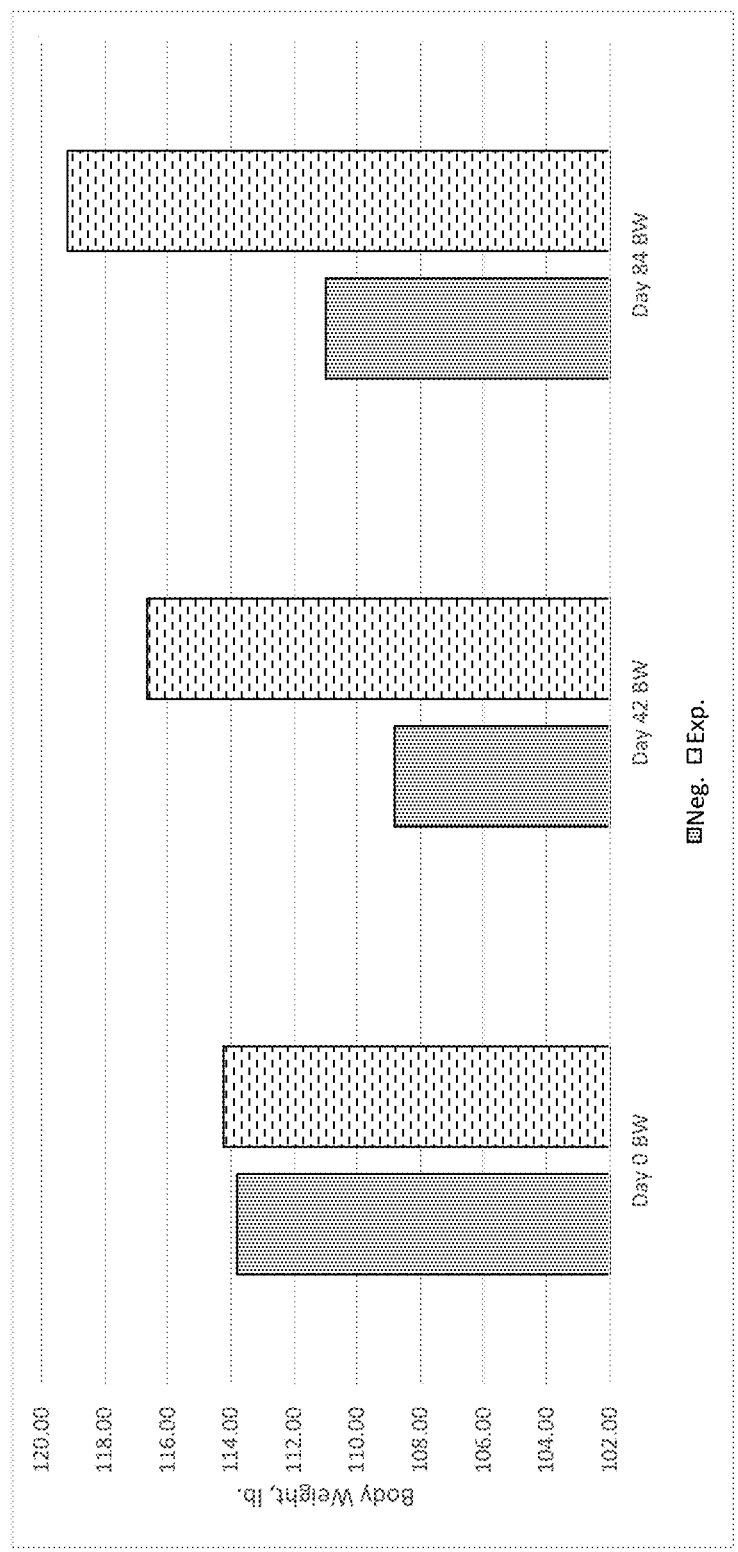
FIG. 1 is a graph showing ruminant body weight measurements during periods of heat stress conditions for ruminants fed a feed composition containing a phytogenic composition and ruminants fed the same feed composition but lacking the phytogenic composition, according to certain implementations.

Systems and methods provide a phytogenic composition in the ruminant diet to improve performance during, or in anticipation of, periods of heat stress. Improved performance may include increased feed intake, weight gain, rib flesh, and/or other indicators of heat stress reduction. Improved performance may be achieved particularly in non-livestock, non-domesticated ruminants, such as deer, during various life stages. By consuming a feed composition that includes a phytogenic composition before or during periods of heat stress, it has been discovered that the ruminants may exhibit improved performance, such as increased weight gain, feed intake, and/or rib flesh compared to heat stressed ruminants not consuming a phytogenic composition, thus ameliorating heat stress symptoms or avoiding them altogether.

According to embodiments disclosed herein, the ruminant animals may include deer. The deer may be non-livestock and/or non-domesticated deer, e.g., white-tail deer. As such, the deer may reside in uncontrolled, outdoor environments, e.g., not covered facilities, where the deer may be free to roam. In some examples, the deer may be bred in captivity and/or confined to outdoor, fenced-in areas. The fenced-in areas may range in size from less than one acre to between 1 and 100 acres or more. In various embodiments, the deer may be considered wild or semi-wild. Wild deer may be deer not conditioned to accept or expect human interaction, while semi-wild deer may be conditioned to accept or expect limited human interaction, e.g., bottle-feeding, hand feeding, and the like. The deer may be adult deer in some examples, but the disclosures provided herein are not limited to specifically aged animals. The deer may also be male or female, and indicators of improved performance may be the same or different between the two sexes. In some embodiments, the deer may be does and may be of approximately breeding age. The term "deer" or "Cervidae" used herein generally means a ruminant mammal of the family Cervidae, including white-tail deer, mule deer, black-tail deer, elk, moose, red deer, caribou, fallow deer, roe deer, pudú, and chital.

Feed Compositions Containing a Phytogenic Composition

Feed compositions of the present disclosure may include a phytogenic composition. In some examples, the feed composition may include a base feed combined with a phytogenic composition. The base feed may include one or more basic nutritional components, and the phytogenic composition may include one or more discrete phytogenic additives.

As disclosed herein, one or more phytogenic additives included in the phytogenic composition may be of plant origin, e.g., plant-derived substances, products, extracts, and/or oils. The specific components of the phytogenic composition may vary and may be adjusted according to the needs and/or condition of the deer, the current or anticipated environmental temperature, and/or the components of the base feed. In embodiments, the phytogenic composition may include one or more active components or substances and one or more carrier components.

In various embodiments, the active components or substances of the phytogenic composition may include but are not limited to: quillaja (soapbark) extract, *curcuma* extract, cayenne pepper, and/or thyme oil. Quillaja extract is a botanical additive derived from the Quillajaceae family of evergreen trees. Pure quillaja extract may be high in saponin content and provided in powdered form in some examples. *Curcuma* extract is a botanical additive derived from the *Curcuma* genus of plants. In some embodiments, *curcuma* extract may include extracts from one or more specific *Curcuma* species, e.g., *Curcuma Longa*. Cayenne pepper may be derived from the *Capsicum annuum* species of peppers. Cayenne pepper may also be provided in powdered form, and may contain high levels of vitamin A. Thyme oil is an herbal oil derived from the *Thymus vulgaris* plant species, a member of the mint family, which may exhibit various antimicrobial properties in some examples. The specific chemical makeup of various types of thyme oil may vary in different embodiments. Embodiments may also include various levels of capsaicin, gingerol and/or piperin. Capsaicin is a chili pepper extract, thus derived from plants in the *Capsicum* genus. Gingerol is the active component of fresh ginger, and may be more accurately referred to as [6]-gingerol. Piperin is an alkaloid, i.e., an organic nitrogen-containing base, which may be extracted from black pepper.

The absolute and relative amounts of each active component may vary. For example, the quillaja extract content of the phytogenic composition may range from about 20 to about 85 wt %, about 25 to about 80 wt %, about 30 to about 75 wt %, about 35 to about 70 wt %, about 40 to about 65 wt %, about 45 to about 60 wt %, or about 50 to about 55 wt % of the phytogenic composition. The *curcuma* content of the phytogenic composition may also vary. In embodiments, the *curcuma* content may range from about 6 to about 26 wt %, about 8 to about 24 wt %, about 10 to about 22 wt %, about 12 to about 22 wt %, about 14 to about 20 wt %, or about 16 to about 18 wt % of the phytogenic composition. The cayenne pepper content of the phytogenic composition may also vary in embodiments, ranging from about 6 to about 26 wt %, about 8 to about 24 wt %, about 10 to about 22 wt %, about 12 to about 22 wt %, about 14 to about 20 wt %, or about 16 to about 18 wt % of the phytogenic composition. The thyme oil content may also vary, ranging in some examples from about 6 to about 26 wt %, about 8 to about 24 wt %, about 10 to about 22 wt %, about 12 to about 22 wt %, about 14 to about 20 wt %, or about 16 to about 18 wt % of the phytogenic composition. In some embodiments, the phytogenic composition may be free of one or more of the active components. In embodiments where one or more components of the phytogenic composition listed above are omitted, the amounts of the remaining components may be increased accordingly, provided that no additional active components replace the omitted component. For example, if one or more active components are omitted, the remaining components may be increased such that the remaining components retain the same relative proportions with respect to each other.

In some embodiments, one or more carrier components may also be included in the phytogenic composition for various purposes. For example, the carrier component(s) may protect the active components from degradation. In addition or alternatively, the carrier component(s) may facilitate digestion of the active components in the ruminant digestive system. The carrier components may be provided as a coating around the active components, or may be integrally mixed with the active components. In some examples, the carrier components may include wheat bran and/or calcium carbonate. The absolute and relative amounts of each carrier component, e.g., wheat bran or calcium carbonate, may vary in different embodiments.

As provided herein, the phytogenic composition may be combined with a base feed in some examples. Together, the phytogenic composition combined with the base feed may comprise a total feed composition fed to ruminant animals according to the disclosed methods. The phytogenic content of the resulting feed composition may vary. For example, in embodiments where the base feed and the phytogenic composition are provided separately and combined by an end user, the phytogenic content may be adjustable. In some examples, the phytogenic content of the total feed composition (containing both the base feed and the phytogenic composition) may range from about 0.005 to about 0.1 wt %, about 0.005 to about 0.2 wt %, about 0.008 to about 0.075 wt %, about 0.008 to about 0.15 wt %, about 0.008 to about 0.064 wt %, about 0.008 to about 0.128 wt %, about 0.01 to about 0.05 wt %, about 0.01 to about 0.1 wt %, about 0.02 to about 0.04 wt %, about 0.02 to about 0.08 wt %, about 0.03 to about 0.035 wt %, or about 0.03 to about 0.07 wt % of the total feed composition. In some embodiments, the phytogenic content of the total feed composition may be varied to target specific ruminants and/or specific feeding spaces. For instance, the phytogenic content of the total feed composition provided to ruminants in high fence and/or pasture areas may range from about 0.005 to about 0.2 wt %, or any of the aforementioned ranges in between. The phytogenic content of the total feed composition fed to ruminants enclosed in penned areas may be lower in some examples, ranging from about 0.005 to about 0.1 wt %, or any of the aforementioned ranges in between.

The base feed may provide the basic nutritional and bulk feed components needed in the ruminant diet. In some examples, the base feed may be the primary food source, by weight, in the ruminant diet, optionally supplemented by other natural food sources, e.g., forages. In embodiments, the physical form and/or composition of the base feed may vary. For example, the base feed may be provided as a pellet. In other embodiments, the base feed may include extruded nuggets, granular mixtures, feed blocks, mineral blocks, feed tubs, paste compositions, liquids, gels, and/or combinations thereof. Accordingly, the texture and moisture level of the base feed may also vary. In some examples, the base feed may be formulated for outdoor feeding. Such formulations may be at least partially weather resistant.

The nutrient profile of the base feed generally includes various amounts of crude protein, crude fat, crude fiber, carbohydrates, and assorted vitamins and minerals, each combined in various amounts to produce a base feed having variable dry matter and moisture content. For example, the total dry matter content of the base feed may range from about 85 to about 99 wt %, about 88 to about 95 wt %, about 90 to about 95 wt %, about 92 to about 94 wt %, or about 93 to about 94 wt % of the base feed. Accordingly, the moisture content may range from about 1 to about 15 wt %, about 5 to about 12 wt %, about 5 to about 10 wt %, about 6 to about 8 wt %, or about 6 to about 7 wt % of the base feed in some examples. Overall crude protein content of the base feed may range from about 10 to about 30 wt %, about 12 to about 25 wt %, about 14 to about 20 wt %, or about 16 to about 18 wt % of the base feed in various embodiments. Total digestible nutrients within the base feed may also vary, ranging in some examples from about 50 to about 80 wt %, about 55 to about 75 wt %, about 60 to about 70 wt %, about 62 to about 68 wt %, or about 64 to about 66 wt % of the base feed. The amount of fat may also vary, ranging in various embodiments from about 1 to about 15 wt %, about 1 to about 10 wt %, about 1 to about 9 wt %, about 2 to about 10 wt %, about 2 to about 8 wt %, about 2 to about 6 wt %, about 1 to about 3 wt %, or about 2 to about 4 wt % of the base feed.

The base feed may include various feed components capable of being blended, mixed or otherwise incorporated with a phytogenic composition. Generally, the feed components should not degrade the phytogenic composition or decrease its effectiveness in treating heat stress (e.g., the feed components should not counteract the effects of the phytogenic composition). In some embodiments, the base feed may include one or more food components including but not limited to: processed grain by-products, roughage products, plant protein products, grain products, molasses products, pellet binders, vegetable oils, salts, calcium carbonate, probiotics, vitamins, minerals, and/or flavoring agents. As disclosed below, the absolute and relative amounts of each base feed component may vary. For consistency, the content of each base feed component is disclosed in the context of the total feed composition, i.e., containing both the base feed and the phytogenic composition.

In embodiments, one or more processed grain by-products may be included in the base feed. The sub-components of the grain by-products may vary depending on the specific grains processed and/or the processes used to capture by-products thereof. In some examples, one or more grain by-products may be included in the base feed in amounts ranging from about 20 to about 55 wt %, about 25 to about 50 wt %, about 30 to about 45 wt %, about 35 to about 40 wt %, or about 37 to about 38 wt % based on the total weight of the feed composition.

Embodiments may also include one or more whole grains, ground grains, or grain components. Where employed in the base feed, a whole grain, ground grain, or a grain component may be a source of carbohydrate, protein, fat, or all of these. Grain components may include bran, germ, endosperm, or portions thereof. Suitable examples of grains may include natural or genetically engineered grains including amaranth, barley, buckwheat, bulgur, corn, einkorn, farro, grano, khorasan grain, kaniwa, millet, oats, quinoa, rice, rye, sorghum, spelt, triticale, wheat (including durum wheat, and bread wheat including hard wheat, soft wheat, white wheat, red wheat, winter wheat, and spring wheat), and wild rice. Where employed in the base feed, the total amount of whole grain, ground grain, or grain components may be present at a total amount of about 5 to about 50 wt % of the feed composition, or about 10 to about 50 wt %, about 10 to about 40 wt %, about 15 to about 30 wt %, or about 20 to about 30 wt % of the total weight of the feed composition, or any compositional amount within the range of about 5 to about 50 wt % in 1 wt % increments (such as 6 wt % to 8 wt %, 16 wt % to 52 wt %, and the like). In particular embodiments, the feed composition may include one or more grain products at amounts ranging from about 1 to about 20 wt %, about 2 to about 15 wt %, about 4 to about 12 wt %, about 5 to about 10 wt %, or about 7 to about 9 wt % of the feed composition.

One or more roughage products may also be included in the base feed in some embodiments. In various examples, the roughage products may contain one or more fibrous materials. The content of the roughage products in the feed composition may vary, ranging from about 5 to about 40 wt %, about 10 to about 35 wt %, about 15 to about 30 wt %, about 20 to about 25 wt %, or about 22 to about 23 wt % based on the total weight of the feed composition.

In some examples, one or more carbohydrates may be provided in the base feed at about 10 to about 90 wt % based on the total weight of the feed composition, or about 15 to about 90 wt %, about 20 to about 90 wt %, about 25 to about 85 wt %, about 30 to about 80 wt %, about 35 to about 80 wt %, about 40 to about 80 wt %, about 45 to about 75 wt %, about 50 to about 75 wt %, or about 50 to 70 wt % based on the total weight of the feed composition, or any compositional amount within the range of about 10 to about 90 wt % in 1 wt % increments (such as 16 wt % to 23 wt %, 84 wt % to 85 wt %, and the like).

Example base feed formulations may also include one or more plant protein products. The content of the plant protein products may vary, ranging from about 3 to about 39 wt %, about 8 to about 34 wt %, about 13 to about 29 wt %, about 18 to about 24 wt %, or about 20 to about 22 wt % based on the total weight of the feed composition.

Where one or more fats are included in the base feed, the one or more fats may be present at about 0.1 to about 10 wt % based on the total weight of the feed composition, about 0.25 to about 9 wt %, about 0.25 to about 8 wt %, about 0.25 to about 7 wt %, about 0.25 to about 6 wt %, about 0.50 to about 6 wt %, about 0.50 to about 5 wt %, about 0.50 to about 4 wt %, about 0.50 to about 3 wt %, or any compositional amount within the range of about 0.1 to about 10 wt % in 0.1 wt % increments (such as 0.3 wt % to 9.7 wt %, 2.6 wt % to 2.7 wt %, and the like).

In various embodiments, one or more plant-derived oils including a vegetable oil, such as palm oil, cottonseed oil, palm kernel oil, and olive oil may be included in the base feed. The amount of plant-derived oils may vary in different examples, ranging from about 0.1 to about 10 wt % of the total weight of the feed composition, or about 0.25 to about 9 wt %, about 0.25 to about 8 wt %, about 0.25 to about 7 wt %, about 0.25 to about 6 wt %, about 0.50 to about 6 wt %, about 0.50 to about 5 wt %, about 0.50 to about 4 wt %, about 0.50 to about 3 wt % based on the total weight of the feed composition, or any compositional amount within the range of about 0.1 to about 10 wt % in 0.1 wt % increments (such as 0.3 wt % to 9.7 wt %, 2.6 wt % to 2.7 wt %, and the like). In particular examples, vegetable oil may be included in amounts ranging from about 0.5 to about 8 wt %, about 1 to about 7 wt %, about 2 to about 6 wt %, about 3 to about 4 wt %, or about 3.3 to about 3.7 wt % based on the weight of the feed composition.

In various embodiments, one or more sugar-containing or sugar-based components may also be included in the base feed. In some examples, sugar-containing components may include molasses, honey, sugarcane, sugar beet, fruit, fruit portions, fruit extracts, and the like. In some embodiments, the sugar containing food source is dried prior to use; for example, molasses or honey may be further dried to remove water prior to use in the base feed compositions of the invention. Where employed, the total amount of sugar-containing food components generally ranges from about 10 to about 90 wt % of the total feed composition. In some embodiments, the sugar-containing food component may be present at about 10 to about 85 wt % based on the total weight of the feed composition, or about 15 to about 80 wt %, about 20 to about 75 wt %, about 20 to about 70 wt %, about 20 to about 65 wt %, about 25 to about 60 wt %, about 25 to about 55 wt %, or about 25 to about 50 wt % based on the total weight of the feed composition or any compositional amount within the range of about 10 to about 90 wt % in 1 wt % increments (such as 16 wt % to 23 wt %, 54 wt % to 75 wt %, and the like). In specific embodiments, the sugar component may include one or more molasses products present in the composition in an amount ranging from about 1 to about 20 wt %, about 1 to about 15 wt %, about 2 to about 13 wt %, about 4 to about 10 wt %, about 5 to about 8 wt %, or about 6 to about 7 wt % based on the weight of the total feed composition.

Another suitable base feed component may be a whole or ground legume, or an extract, or component thereof, including the oil thereof, and combinations of two or more thereof. Where employed in the base feed, a whole or ground legume, or an extract, or component thereof may be a source of carbohydrate, protein, fat, or all of these. Examples of suitable legumes may include peanuts, chickpeas, various common strains of beans and peas, fava beans, lentils, lima beans, lupins, mung beans, pigeon peas, runner beans, and soybeans. The total amount of whole or ground legume, or an extract, or component thereof generally may range from about 1 to about 75 wt % based on the total weight of the feed composition, about 5 to about 60 wt %, or about 10 to about 50 wt % based on the total weight of the feed composition, or any compositional amount within the range of about 1 to about 75 wt % in 1 wt % increments (such as 6 wt % to 23 wt %, 56 wt % to 68 wt %, and the like).

In some embodiments, another suitable food component may be a whole or ground seed or an extract, or component thereof, including the oil thereof, and combinations of two or more thereof. Where employed in the base feed, a whole or ground seed or an extract, or component thereof may provide a source of carbohydrate, protein, fat, or all of these. Examples of suitable seeds may include flax seed, safflower seed, sunflower seed, rapeseed including canola, and the like. The total amount of whole or ground seed or an extract, or component thereof generally ranges from about 1 to about 50 wt % based on the total weight of the feed composition, about 5 to about 40 wt %, or about 10 to about 50 wt % based on the total weight of the feed composition, or any compositional amount within the range of about 1 to about 50 wt % in 1 wt % increments (such as 6 wt % to 23 wt %, 54 wt % to 55 wt %, and the like).

Another suitable food component may be one or more minerals. In some examples, minerals may include compounds such as monocalcium phosphate, dicalcium phosphate, calcium carbonate, sodium carbonate, sodium bicarbonate, sodium chloride, potassium chloride, potassium carbonate, potassium iodate, magnesium oxide, ferric oxide, ferrous oxide, calcium oxide, calcium hydroxide, chromic oxide, copper oxide, copper sulfate, zinc oxide, calcium chloride, copper sulfate, trace amounts of selenium, chromium, cobalt, molybdenum, manganese, fluoride, iodine, and the like. In particular embodiments, calcium carbonate may be included in the base feed in amounts ranging from about 0.25 to about 5 wt %, about 0.5 to about 4 wt %, about 0.75 to about 3 wt %, about 1 to about 2 wt %, or about 1.25 to about 1.75 wt % based on the total weight of the feed composition. Some examples may include vitamins such as vitamin A, K, D, D3, various B vitamins, or vitamin E. In various embodiments, one or more vitamins may be mixed with one or more minerals, forming a mineral/vitamin premix. In such examples, the premix may be included in the feed composition in amounts ranging from about 0.01 to about 0.5 wt %, about 0.04 to about 0.4 wt %, about 0.08 to about 0.3 wt %, about 0.1 to about 0.2 wt %, or about 0.13 to about 0.17 wt % of the total feed composition.

Embodiments may also include one or more probiotics. In some examples, the probiotic content may range from about 0.01 to about 2 wt %, about 0.01 to about 1 wt %, about 0.05 to about 0.5 wt %, about 0.1 to about 0.2 wt %, or about 0.14 to about 0.16 wt % of the feed composition.

In some embodiments, one or more binders, preservatives, stabilizers, emulsifiers, palatants (palatability enhancers), attractants, and combinations of two or more thereof may be suitably included in the base feed. The additives may be food safe for the selected animal.

For instance, where the base feed is in a pelleted form, one or more pellet binders may be included. The pellet binders may be formulated to increase the cohesiveness of each separate base feed pellet. The content of one or more binders within the feed composition may vary, ranging from about 0.5 to about 8 wt %, about 1 to about 6 wt %, about 2 to about 4 wt %, about 2.5 to about 3.5 wt %, or about 2.8 to about 3.2 wt % of the total feed composition.

Flavoring agents included in the base feed may also vary in identity and/or content. In embodiments, flavoring agents may include a single flavor-enhancing component or a combination of multiple components. The content of flavoring agents may vary, ranging from about 0.005 to about 0.05 wt %, about 0.01 to about 0.03 wt %, or about 0.015 to about 0.025 wt % of the total feed composition.

Examples of suitable preservatives may include one or more of sorbic acid, potassium sorbate, fumaric acid, propionic acid, and benzoic acid. Antimicrobial preservatives may include sorbic acid and its salts, benzoic acid and its salts, calcium propionate, sodium nitrite, sulfites (sulfur dioxide, sodium bisulfite, potassium hydrogen sulfite, etc.) and disodium EDTA. Antioxidants may include BHA, BHT, TBHQ and propyl gallate. Other preservatives may include ethanol and methylchloroisothiazolinone. Naturally occurring substances such as rosemary extract, hops, salt, sugar, vinegar, alcohol, diatomaceous earth and castor oil are also useful as preservatives in some embodiments of the base feed. In particular embodiments, one or more salts may be present in the feed composition in amounts ranging from about 0.1 to about 5 wt %, about 0.2 to about 4 wt %, about 0.3 to about 3 wt %, about 0.4 to about 2 wt %, about 0.5 to about 1 wt %, or about 0.7 to about 0.8 wt % of the total feed composition.

Examples of suitable emulsifiers may include egg yolk lecithin, mustard seed mucilage, soy lecithin, sodium stearoyl lactylate, and monoglyceride ester of diacetyl tartaric acid.

Suitable stabilizers may include those that prevent undesirable interactions within the components of the base feed and/or one or more components of the phytogenic composition mixed therewith. For example, calcium sequestrants such as tetrasodium pyrophosphate may be usefully employed to prevent interaction of calcium ions with other components of the base feed and/or phytogenic composition compositions, thereby maintaining stability of the feed.

Methods of Feeding Feed Compositions Containing a Phytogenic Composition

Methods of feeding ruminant animals may involve feeding the animals a feed composition containing a phytogenic composition in a manner effective to improve performance during, or in anticipation of, periods of heat stress. This approach may involve obtaining a phytogenic composition and combining it with a base feed prior to feeding. Alternatively, the base feed may already contain the phytogenic composition such that end-mixing is unnecessary.

According to certain implementations, a feed composition containing a phytogenic composition may be provided to the ruminant animals, e.g., non-livestock, non-domesticated ruminant animals, in anticipation of periods of heat stress and/or during of periods of heat stress. Heat stress conditions may generally include elevated temperatures and/or humidity levels. In some examples, ruminant animals may be more vulnerable to heat stress during abnormally warm and/or humid conditions, versus warm and/or humid conditions that coincide with seasonal expectations. In some examples, heat stress conditions may include ambient temperature conditions of at least about 70° F. In other examples, heat stress conditions may include ambient temperature conditions of at least 75° F., 80° F., 85° F., 90° F., 95° F., 100° F. or above. The duration of high ambient temperatures necessary to cause heat stress may vary. For example, heat-stress conditions lasting less than one day may be sufficient to cause heat stress in one or more ruminant animals. In some examples, heat stress conditions may persist for more than one day, e.g., two or more days or one or more weeks, before heat stress symptoms develop.

During a period of heat stress conditions, an end user may determine that one or more ruminant animals are experiencing heat stress. An end user may make this determination by observing one or more symptoms indicative of heat stress. Symptoms may be physical and/or behavioral. For example, heat stress may be observed in the ruminants by one or more symptoms including increased respiratory rates, decreased activity levels, decreased dry matter or feed intake, elevated internal body temperature, open mouth breathing, excessive panting, sweating, and failed reproduction. An end user may also determine that a potential for heat stress is increased. In some examples, environmental heat stress may be predicted based historical weather patterns and/or short-term weather forecasting. For instance, a potential for heat stress may be predicted based on an upcoming seasonal change, e.g., from spring to summer. In other examples, a potential for heat stress may be predicted based on a short-term weather forecast predicting a sudden onset of warmer temperatures, e.g., in two weeks or less.

After determining either that a ruminant animal is experiencing heat stress or that a potential for heat stress exists, the ruminant animal may be fed a feed composition that includes a phytogenic composition according to any of the formulations disclosed above. The amount of the phytogenic composition consumed by the ruminant may be effective to improve performance. During periods of time where the potential for heat stress is elevated, inclusion of the phytogenic composition in a base feed may also be beneficial to avoid or delay the onset of heat stress symptoms, or at least reduce the severity of such symptoms should they still occur.

In embodiments, the provision of a feed composition containing a phytogenic composition may begin immediately upon determining that one or more ruminants exhibit symptoms of heat stress. Proactively feeding ruminants such feed compositions after identifying a potential for heat stress conditions may commence, in various embodiments, at different lengths of time prior to the arrival of heat stress conditions. For example, ruminants may be provided with the feed composition during the spring, in anticipation of warmer summer temperatures. In other examples, the feed composition may be provided to ruminants for about two weeks or less before the onset of heat stress conditions in response to a short-term weather forecast. Thus, the feed composition may be incorporated into the ruminant diet on a regular basis, e.g., every spring and/or summer, or on an intermittent basis, e.g., in response to weather forecasting. In some embodiments, the feed composition may be provided in the diet both before and during periods of heat stress conditions. One or more metrics of improved performance may be enhanced in such embodiments compared to examples in which the deer is fed the feed compositions exclusively before or during periods of heat stress conditions.

Generally, ruminant animals may be offered a feed composition containing a phytogenic composition ad libitum on a daily basis. In such embodiments, the animals may be provided the feed composition from a self-feeder apparatus. In addition or alternatively, the feed composition may be deposited or dispersed in one or more outdoor areas where the ruminant animals may typically roam. In alternative implementations, the ruminant animals may be offered a fixed daily amount of the feed composition containing a phytogenic composition, which may form all or a portion of the animals' daily feed ration.

In some examples, the base feed and the phytogenic composition may be provided to end users in separate containers or packages. In such embodiments, the user may be instructed to mix the base feed with the phytogenic composition according to one or more instructions provided on the packaging for the base feed and/or the phytogenic composition. Instructions may indicate acceptable amounts of phytogenic composition to be admixed with various amounts of base feed. Instructions may also provide methods of adjusting the phytogenic content of the feed composition in response to variations in the severity of heat stress conditions. For example, the instructions may advise end users to increase the phytogenic content of the feed composition (by adding more of the phytogenic composition to the base feed) during periods of extreme heat. The instructions may also indicate acceptable time frames to begin feeding ruminants in anticipation of heat stress conditions. For example, the instructions may advise end users to begin providing feed compositions mixed with the phytogenic composition to ruminants at least two weeks prior to the anticipated onset of heat stress conditions. In some embodiments, the instructions may include one or more warning signs, e.g., heat stress symptoms, prompting end users to begin mixing the phytogenic composition with the base feed and providing the resulting feed composition to the ruminants. In addition or alternatively, the instructions may provide one or more average temperature ranges that place ruminants at a heightened risk of experiencing heat stress. In some embodiments, the temperature ranges may vary by geographic location, such that the temperature ranges associated with heat stress in warmer climates are higher than typical heat-stress temperatures in cooler climates. Such instructions may avoid over- or underuse of the phytogenic compositions due to variations in heat tolerance exhibited by ruminant animals accustomed to different living conditions.

The amount of phytogenic composition fed to and available for consumption by the ruminant animals may vary. In some examples, the amount of phytogenic composition necessary to improve the performance of one or more ruminant animals may also vary. For instance, increased phytogenic content may be required to improve performance during excessively warm conditions, e.g., 85° F. or above, or increased levels of the phytogenic composition may be loaded in the feed for high fence or pasture deer that consume less of the feed composition by virtue of having access to natural forages, e.g., plants, leaves, grasses, compared to pen deer. In some embodiments, ruminant animals may be fed about 50 to about 3000 mg, about 100 to about 2500 mg, about 200 to about 2200 mg, about 300 to about 2000 mg, about 400 to about 1800 mg, about 500 to about 1600 mg, about 600 to about 1400 mg, about 700 to about 1300 mg, about 800 to about 1200 mg, about 900 to about 1100 mg, about 50 to about 1500 mg, about 100 to about 1250 mg, about 200 to about 1250 mg, about 300 to about 1000 mg, about 400 to about 900 mg, about 500 to about 800 mg, about 600 to about 700 mg, about 100 to about 3000 mg, about 200 to about 2500 mg, about 400 to about 2200 mg, about 600 to about 2000 mg, about 800 to about 1800 mg, about 1000 to about 1600 mg, about 1200 to about 1400 mg, or about 1250 to about 1350 mg of the phytogenic composition per head per day.

The amount of total feed composition, including the phytogenic composition, fed to and available for consumption by the ruminant animals may also vary. In some examples, ruminant animals may be fed about 0.5 to about 10 lbs., about 1 to about 7 lbs., about 2 to about 5 lbs., about 3 to about 4 lbs., about 3.5 to about 4 lbs., about 3.75 to about 3.9 lbs., about 2.5 to about 3 lbs., or about 2.75 to about 2.9 lbs. of the feed composition per head per day.

In various implementations and alternatives, one or more ruminant animals may be fed the feed compositions containing the phytogenic composition on a consistent, e.g., daily, basis at least until heat stress conditions and/or symptoms subside. In some embodiments, one or more ruminants may be fed the feed compositions for a period of time after the disappearance of heat stress conditions to prevent a reemergence of one or more heat stress symptoms.

The methods of feeding disclosed herein may improve the performance of ruminant animals during, or in anticipation of, conditions of heat stress. Indicators of improved performance may vary from animal to animal, and may depend on various factors including animal age, animal sex, and/or the severity of heat stress symptoms exhibited by the animal prior to feeding according to the methods disclosed herein. In embodiments, improved performance may relate to a direct reversal of one or more heat stress symptoms and/or improvements to animal health not directly tied to a reduction in heat stress, but improvements that might not otherwise occur during periods of heat stress.

In some examples, improved performance may include increased body weight. In particular, ruminant animals fed a feed composition containing a phytogenic composition during periods of heat stress may gain more weight than ruminant animals fed an identical feed composition but without the phytogenic composition. In some examples, ruminants fed the phytogenic composition may at least maintain an approximately consistent body weight during periods of heat stress, while ruminants not fed the phytogenic composition may lose weight during the same period. In some examples, ruminants fed a feed composition containing a phytogenic composition according to the methods disclosed herein may gain, on average, at least about 0.5 to about 2.52 lbs., about 1 to about 2.52 lbs., or about 2 to about 2.5 lbs. over a period of heat stress conditions lasting about 40 to about 45 days. In some embodiments, ruminants fed a feed composition containing a phytogenic composition may gain up to approximately 0.06 lbs. per day during a period of heat stress. By contrast, ruminant animals fed the same feed composition, e.g., base feed, but lacking phytogenic supplementation may lose weight over the same time period. For example, such animals may lose about 1 to about 5 lbs. over a period of heat stress conditions lasting about 40 to about 45 days.

In some embodiments, improved performance may include improvements in body mass and/or composition. One indicator of body mass/composition for ruminants is rib flesh, which may generally refer to the amount and/or nature of flesh in the area of a ruminant's ribs. Lower amounts of rib flesh may be indicative of decreased body mass, while greater amounts of rib flesh may be indicative of increased body mass, e.g., body fat and/or skeletal muscle. Improved rib flesh may be indicative of general health improvements. For instance, an increase in rib flesh content may reflect higher activity levels of a ruminant in some examples, and/or increases in feed intake and overall weight gain.

Under conditions of heat stress, ruminants not fed phytogenic additives may exhibit lower amounts of rib flesh, which may continue to decrease as heat stress conditions continue. By contrast, ruminants fed according to the methods herein may sustain a constant level of rib flesh, or even show rib flesh gains during periods of heat stress.

According to the disclosures herein, improved performance may also include increased feed intake. In particular, ruminants fed a feed composition that includes the disclosed phytogenic composition may exhibit greater levels of feed intake during periods of heat stress than animals fed an identical feed composition but without the phytogenic composition during periods of heat stress. In particular examples, ruminants offered feed compositions containing a phytogenic composition may consume up to about 30% more feed per day than animals offered the same feed composition but without the phytogenic composition. In embodiments, the increase in daily feed intake observed in ruminants fed the phytogenic composition versus ruminants not fed the phytogenic composition may range from about 1 to about 10%, about 10 to about 20%, or about 20 to about 30%. In some examples, ruminants fed a feed composition containing a phytogenic composition may consume between about 3 and about 3.73 lbs. of feed per head per day, while ruminants not fed a phytogenic composition with an otherwise identical feed composition may consume only about 2.5 to about 2.88 lbs. of feed per head per day. The difference in feed intake observed between animals fed phytogenic compositions during heat stress periods and those not offered phytogenic compositions may increase or decrease as heat stress conditions persist. For example, the longer heat stress conditions persist, the greater the difference in observed feed intake between ruminants fed according to the methods herein and those not fed according to the methods herein.

In some examples, one or more indicators of improved performance may vary depending on the sex of the animal. For example, feeding male ruminants according to the methods discussed herein may promote antler growth and/or health during periods of heat stress.

Methods of Making Feed Compositions Containing a Phytogenic Composition

In various embodiments, the feed compositions disclosed herein may be formed by employing known industrial techniques and equipment. Both batch and continuous modes of manufacturing are advantageously employed by those of skill in the art to make variously-formulated base feeds, phytogenic compositions, and compositions thereof.

The manner and timing by which the base feed compositions are combined with the phytogenic compositions may vary. For instance, the phytogenic composition may be admixed with the base feed. In such examples, both the phytogenic composition and base feed may be fully formed prior to mixing. In other embodiments, the phytogenic composition may be integrally formed with the base feed or components thereof, e.g., during an extrusion process, such that the base feed is not yet fully formed upon phytogenic addition thereto.

Implementations of the present disclosure are more particularly described in the following ruminant trials that are for illustrative purposes only. Numerous modifications and variations are within the scope of the present disclosure as will be apparent to those skilled in the art.

In the Examples below, statistical analysis was completed for parameters studied such as body weight, body weight gain, rib flesh, and feed intake. A P-value of 0.10 means that 10 times out of 100 the result can be explained by factors other than the feeding of phytogenic additives verses the lack of phytogenic feeding. Statistical analysis was performed using SAS version 9.4 with pen identified as the experimental unit. PROC MIXED was used to analyze body weight, body weight gain, and feed consumption. PROC NPAR1WAY was used to analyze rib flesh score as a Wilcoxon analysis. Statistically significant differences are designated as those having a P-value of 0.2 or less, meaning that the differing results may be explained by the test regimen, i.e.: the feeding of a base feed that includes a phytogenic composition versus the feeding of the base feed alone.

EXAMPLES

Non-Livestock Ruminant Animal Trial 1

This study was conducted to assess the impact of phytogenic feed additives on heat-stressed deer. Multiple performance parameters were tracked to measure deer performance, including body weight, body weight gain, rib flesh score, and total feed consumption. By observing the effects of feeding phytogenic feed additives during periods of heat-stress conditions, this study revealed the significant improvements in deer performance that may be achieved by feeding deer according to the methods disclosed herein.

At a deer facility near Canadian, Tex., 67 breeding age, white-tailed does were stratified by pregnancy status and each allocated randomly to one of six equally-sized treatment pens. Three pens were used for each treatment, and all does present within the same pen received the same treatment over the 84-day trial period beginning Jun. 23, 2016 and ending Sep. 15, 2016.

On day zero of the trial, a complete base feed was provided to all deer on an ad libitum basis from a self-feeder apparatus. Deer in the negative control group were fed only the base feed, and deer in the experimental group were fed the base feed supplemented with a phytogenic feed additive composition sourced from Delacon Biotechnik GmbH. The feed provided to each group was replenished on a weekly basis throughout the trial. The specific components of the feed compositions provided to each group, and their relative amounts, are shown below in Table 1. Deer body weight was measured individually using a Delclayna Tunnel System with an electronic scale (EziWeigh5i, TruTest Inc., Mineral Wells, Tex.). Rib flesh score was also determined individually by a trained evaluator using a numeric scale ranging from 1 to 5: 1=poor; 2=lean; 3=prime; 4=heavy; and 5=obese.

TABLE 1

Feed Composition Formulas

| | Content Range | |
|---|---|---|
| Feed Component | Negative Control | Experimental |
| Processed Grain By Products | 35%-40% | 35%-40% |
| Roughage Products | 20%-25% | 20%-25% |
| Plant Protein Products | 18%-24% | 18%-24% |
| Grain Products | 5%-10% | 5%-10% |
| Molasses Products | 5%-8% | 5%-8% |
| Pellet Binder | 2%-4% | 2%-4% |
| Vegetable Oils | 3%-4% | 3%-4% |
| Salt | 0.5%-1% | 0.5%-1% |
| Calcium Carbonate | 1%-2% | 1%-2% |
| Probiotics | 0.1%-0.2% | 0.1%-0.2% |

TABLE 1-continued

Feed Composition Formulas

| Feed Component | Content Range | |
| --- | --- | --- |
| | Negative Control | Experimental |
| Vitamin/Mineral Premix | 0.1%-0.2% | 0.1%-0.2% |
| Flavoring Agents | 0.01%-0.03% | 0.01%-0.03% |
| Delacon Phytogenic Compound | 0% | 0.05%-0.2% |

After day zero, body weight and rib flesh scores were measured on day 42 and again on day 84 of the trial. Body weight gain was determined for the interim periods and at the end of the trial period. To monitor heat-stress conditions, daily temperatures were retrieved from the N.O.A.A. weather database for Hemphill County Airport, Canadian Tex.

FIG. 1 shows the average body weight for the negative control group and the experimental group. Average body weight is displayed on the y-axis, and time is displayed on the x-axis. As shown in FIG. 1, there was no statistically significant difference in body weight between the two treatment groups on day zero (P-value=0.96). On day 42, however, a significant difference in body weight between the two treatment groups was measured (P-value=0.19). In particular, the day-42 average body weight of each deer in the negative control group was 109.0 lbs., while the average body weight per deer for the experimental group was 119.5 lbs. A significant difference in body weight between the negative control group and the experimental group was also measured on day 84 of the trial (P-value=0.18). On day 84, each deer in the negative control group averaged 111.0 lbs., and the each deer in the experimental group averaged 119.5 lbs. Thus, at the mid- and end-points of the trial, the experimental group of deer fed the base feed plus a phytogenic additive composition had increased average body weight relative the negative control group fed the same base feed but lacking any phytogenic additives.

Figure 2:
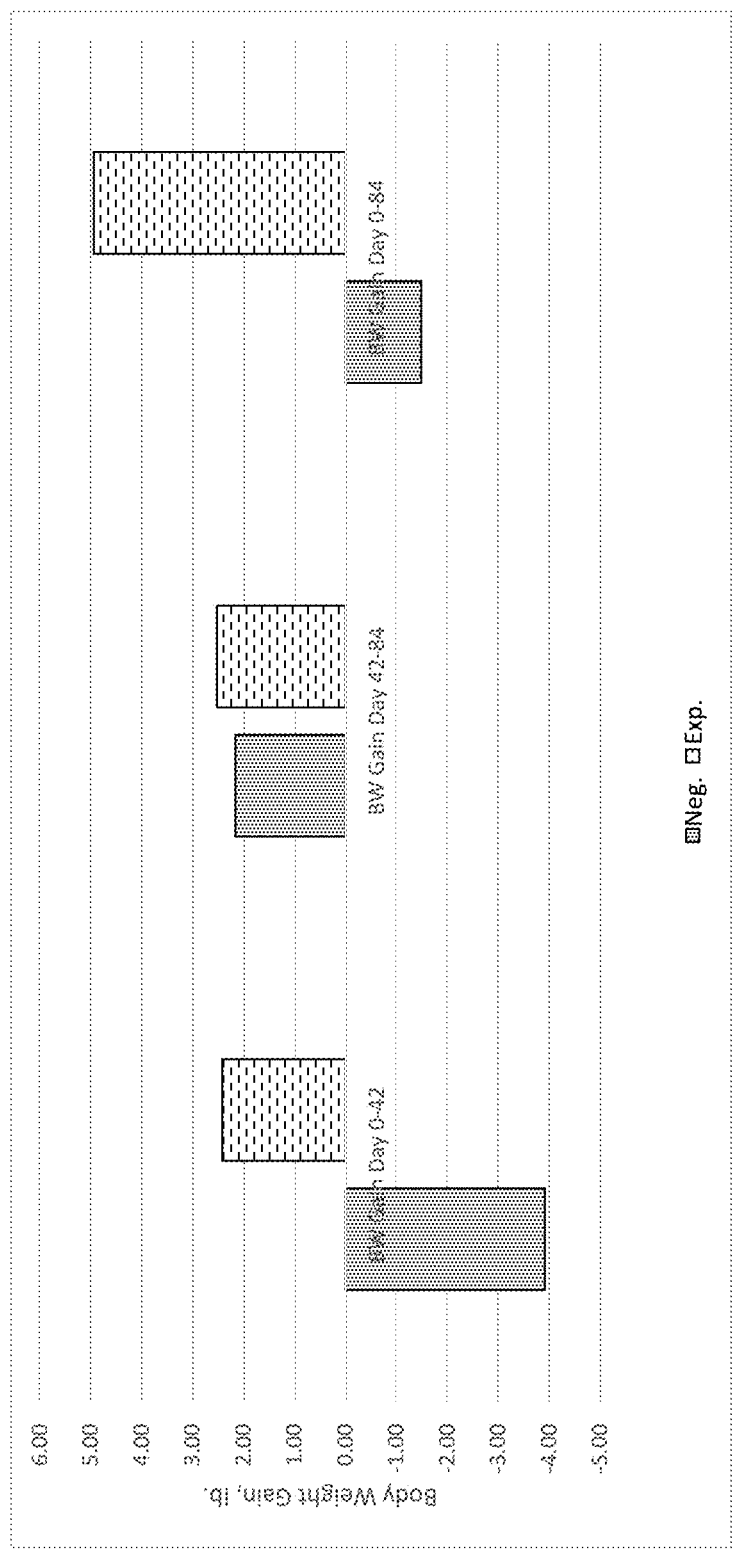
FIG. 2 is a graph showing changes in ruminant body weight measured during periods of heat stress conditions for the ruminants represented in FIG. 1, according to certain implementations.

FIG. 2 shows the average body weight gain for the negative control group, not fed the phytogenic additives, and the experimental group, fed the phytogenic additives. The y-axis shows per-deer average body weight gains, with positive values representing increases in average body weight, and negative values representing decreases in average body weight. As shown in FIG. 2, average body weight gain between day zero and day 42 was −3.87 pounds for the negative control group and +2.52 pounds for the experimental group, representing a significant difference in body weight gain between the negative control animals and the experimental animals (P=0.19). A numerical difference in body weight gain was also observed over the total trial period. In particular, average body weight gain was −1.45 pounds for the negative control group and +5.00 pounds for the experimental group over the period spanning from day zero to day 84. Thus, feeding deer a base feed supplemented with phytogenic additives during a period of heat stress conditions resulted in an increase in body weight gain compared to deer fed an identical base feed, but without the phytogenic additives.

Figure 3:
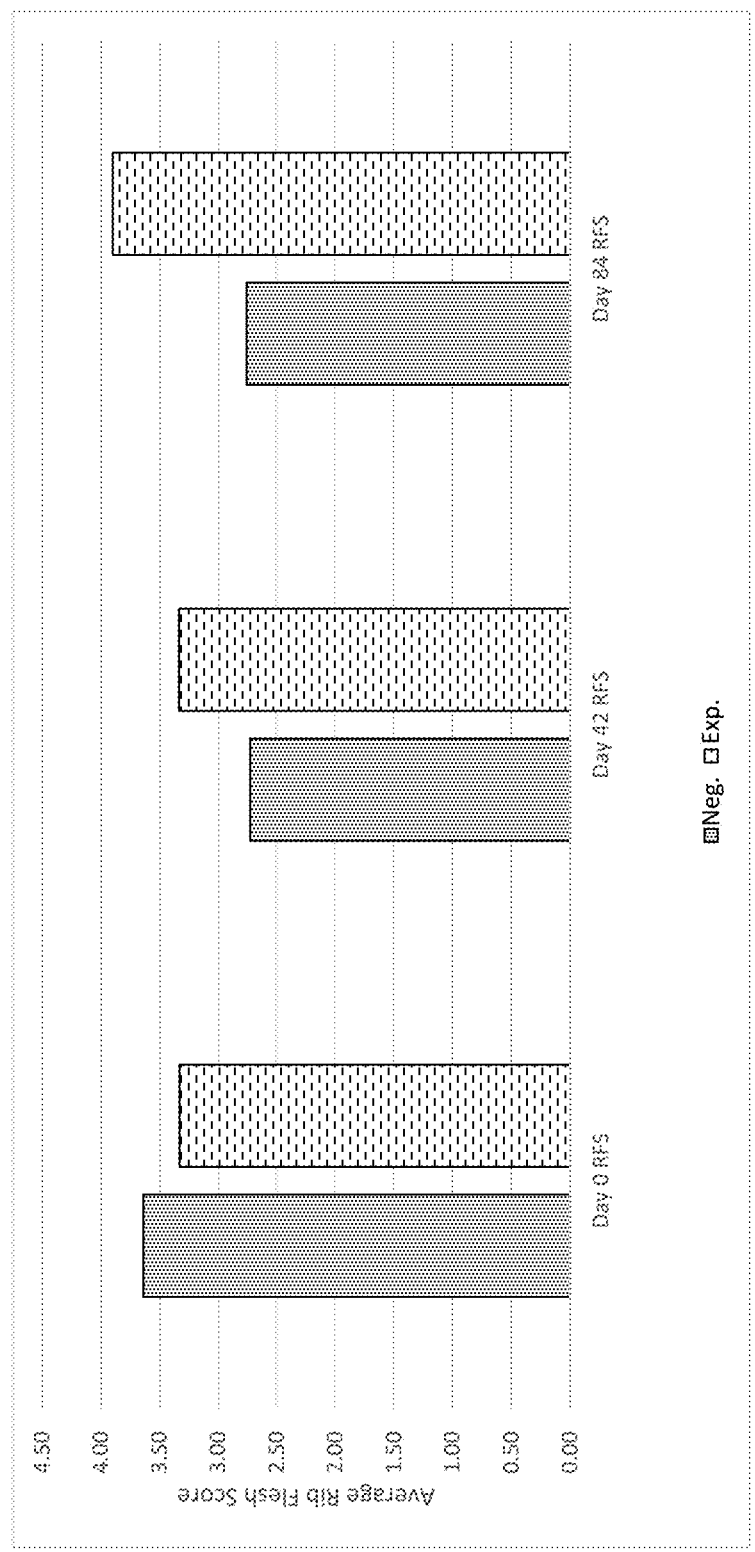
FIG. 3 is a graph showing ruminant rib flesh scores during periods of heat stress conditions for the ruminants represented in FIGS. 1 and 2, according to certain implementations.

FIG. 3 shows the average rib flesh score for the negative control group and the experimental group. The y-axis shows average rib flesh score on a numerical scale ranging from 1 (poor) to 5 (obese). The x-axis displays time. As shown in FIG. 3, rib flesh scores at day zero were not significantly different between treatment groups. On days 42 and 84, however, rib flesh scores for the experiment group were higher than rib flesh scores for the negative control group, producing P-values of 0.06 and less than 0.01, respectively. In particular, rib flesh scores for the experimental group remained above 3.0 for the 84-day duration of the trial, approaching a score near 4.0 by day 84. The negative control animals showed a noticeable decrease in rib flesh score, dipping below 3.0 by day 42, and remaining below 3.0 through day 84. Accordingly, animals in the experimental group exhibited improved rib flesh compared to the negative control group. Improved rib flesh may be indicative of general increases in body mass, reflecting increased body fat and/or muscle content.

Figure 4:
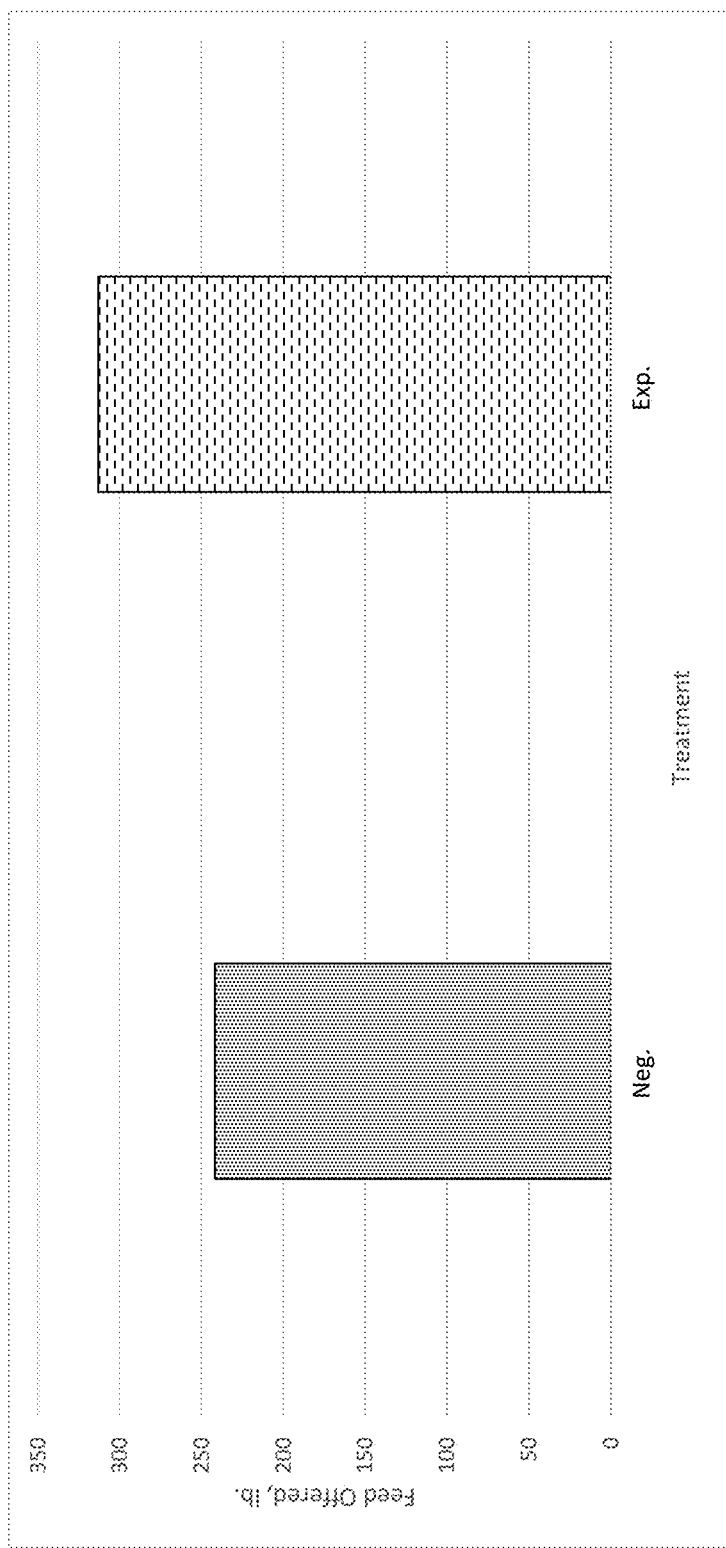
FIG. 4 is a graph showing the average feed offered per ruminant during periods of heat stress conditions for the ruminants represented in FIGS. 1-3, according to certain implementations.

FIG. 4 shows the average feed offered per deer in the negative control group and experiment group over the 84-day duration of the trial. As shown, deer in the negative control group were offered, on average, 242.1 pounds of feed. Deer in the experimental group were offered 313.4 pounds of feed. Because the deer in each of the treatment groups were offered feed via a self-feeder apparatus on an ad libitum basis that was replenished weekly, the greater amount of feed offered to the deer in the experimental group indicates increased feed intake compared to the negative control animals. The results represent an approximately 30% increase in total feed intake over the trial period exhibited by animals offered a feed composition including phytogenic additives. These results correspond to an average daily intake of about 3.73 lbs. for the experimental animals versus an approximately 2.88 lb. average for the negative control animals. Accordingly, the results shown in FIG. 4 demonstrate that feeding deer a base feed supplemented with phytogenic additives during a period of heat stress results in an increase in feed intake compared to deer fed an identical base feed, but without the phytogenic additives.

Figure 5:
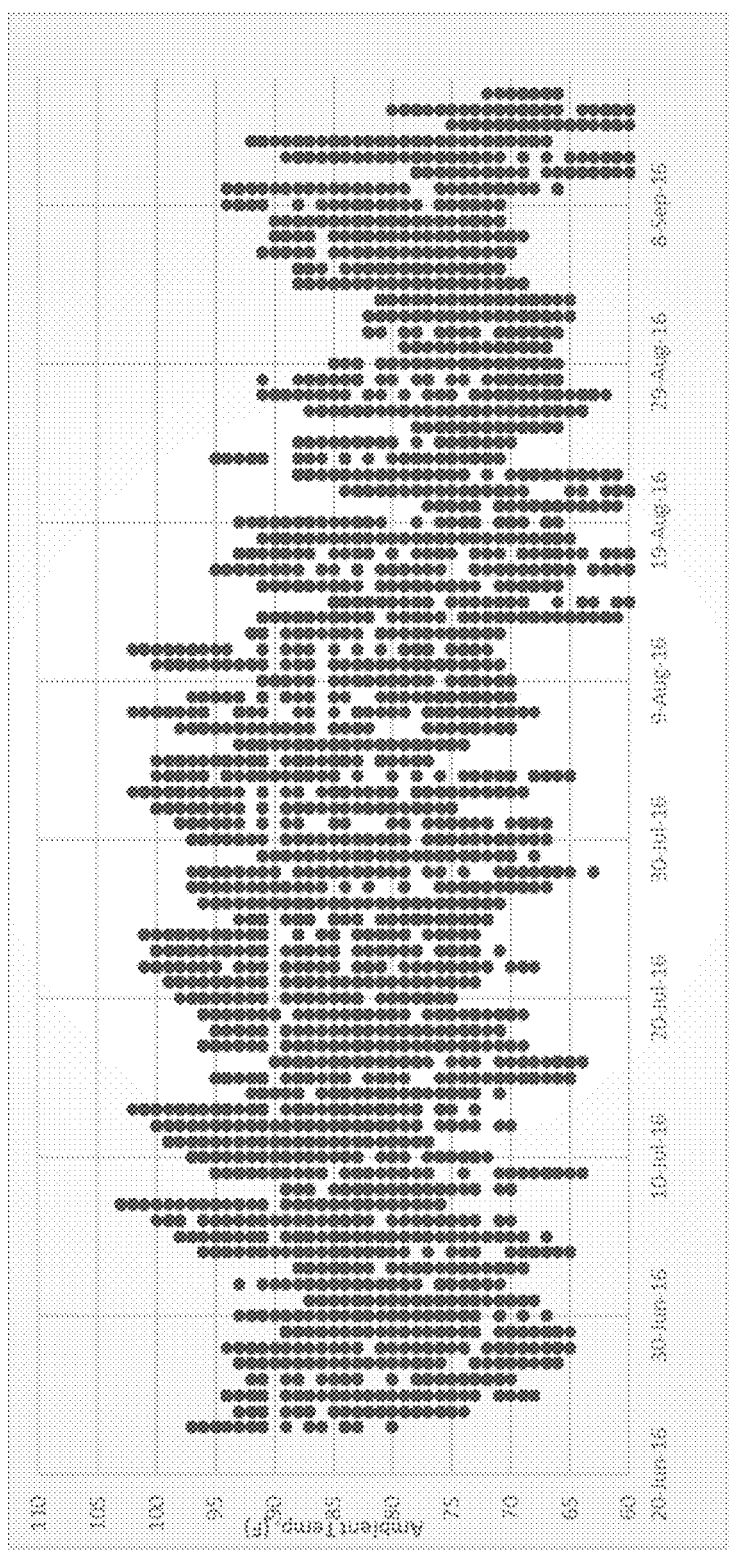
FIG. 5 is a graph showing ambient temperatures measured daily during the periods of heat stress represented in FIGS. 1-4.

FIG. 5 shows the ambient temperatures measured at the trial site, recorded every 15 minutes over the 84-day trial period. Each dot shown in FIG. 5 represents a discrete temperature point, with only different temperatures shown. Thus, a constant temperature recorded every 15 minutes for an entire day would be represented by a single dot for that day. Each column of dots represents temperatures recorded during a single day. As shown, temperatures over the trial period ranged from about 60° F. to over 100° F. The temperature met or exceeded 85° F. at least once on 74 different days. The temperature met or exceeded 90° F. at least once on 62 different days, and met or exceeded 95° F. at least once on 35 different days. On average, the temperature was higher over day 0 to day 42 than from day 42 to day 84. Accordingly, the improvements in performance noted above, e.g., increased weight, increased weight gain, improved rib flesh score and/or increased feed intake, may have been even more substantial had temperatures remained consistently high throughout the entire trial period.

Overall, the breeding does receiving the phytogenic feed additives in their diet consumed more feed, gained more body weight, and had increased rib flesh scores during the 84-day trial period.

As used herein, the term "about" modifying, for example, the quantity of a component in a composition, concentration, and ranges thereof, employed in describing the embodiments of the disclosure, refers to variation in the numerical quantity that can occur, for example, through typical measuring and handling procedures used for making compounds, compositions, concentrates, or use formulations; through inadvertent error in these procedures; through differences in the manufacture, source, or purity of starting materials or components used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

Similarly, it should be appreciated that in the foregoing description of example embodiments, various features are sometimes grouped together in a single embodiment for the purpose of streamlining the disclosure and aiding in the understanding of one or more of the various aspects. These methods of disclosure, however, are not to be interpreted as reflecting an intention that the claims require more features than are expressly recited in each claim. Rather, as the following claims reflect, inventive aspects lie in less than all features of a single foregoing disclosed embodiment, and each embodiment described herein may contain more than one inventive feature.

Although the present disclosure provides references to preferred embodiments, persons skilled in the art will recognize that changes may be made in form and detail without departing from the spirit and scope of the invention.

What is claimed is:

1. A method of improving performance of a non-livestock ruminant animal in heat stress comprising:
   (a) determining that the animal is in heat stress during a period of heat stress, and
   (b) feeding to the animal in heat stress an effective amount of a feed composition containing about 0.05 to about 0.2 wt % of a phytogenic composition,
wherein the phytogenic composition comprises effective amounts of thyme oil and at least one compound selected from the group consisting of guilluja, *curcuma* and cayenne pepper, and
wherein the non-livestock ruminant animal is a non-domesticated animal of the family Cervidae.

2. The method of claim 1, further comprising identifying the period of heat stress conditions based on one or more of weather patterns or short-term weather forecasts.

3. The method of claim 1, wherein the period of heat stress comprises an ambient temperature of at least 70° F.

4. The method of claim 1, wherein determining that the non-livestock ruminant animal is in heat stress comprises observing at least one of a decrease in feed intake, reduced activity levels, open mouth breathing, increased panting, sweating, or reduced reproduction.

5. The method of claim 1, wherein the phytogenic composition is fed at a rate of about 100 milligrams to about 1500 milligrams per ruminant per day.

6. The method of claim 1, wherein improved performance comprises one or more of increased body weight, increased rib flesh, or increased feed intake.

7. The method of claim 1, wherein improved performance comprises an approximately 30 percent increase in daily feed intake compared to a non-livestock ruminant animal not fed the feed composition.

8. The method of claim 1, wherein the non-livestock ruminant animal is an adult white-tailed deer.

9. The method of claim 1, wherein the non-livestock ruminant animal is a breeding-age doe.

10. The method of claim 1, wherein the feed composition further comprises a base feed, the base feed comprising one or more of processed grain by-products, roughage products, plant protein products, grain products, molasses products, pellet binders, vegetable oils, salt, calcium carbonate, probiotics, flavoring agents, vitamins, or minerals.

11. The method of claim 10, wherein the base feed and the phytogenic composition are mixed together by an end user to form the feed composition.

12. The method of claim 10, wherein prior to the step of feeding, the base feed and the phytogenic composition are integrally mixed.

13. The method of claim 1, wherein feeding the non-livestock ruminant animal the feed composition comprises providing the feed composition on an ad libitum basis.

* * * * *